(12) United States Patent
Tuschl et al.

(10) Patent No.: US 7,416,842 B2
(45) Date of Patent: Aug. 26, 2008

(54) DNA VIRUS MICRORNA

(75) Inventors: Thomas H. Tuschl, New York, NY (US); Sebastien Pfeffer, New York, NY (US)

(73) Assignee: The Rockefeller University, New York, NY (US)

( * ) Notice: Subject to any disclaimer, the term of this patent is extended or adjusted under 35 U.S.C. 154(b) by 444 days.

(21) Appl. No.: 10/819,098

(22) Filed: Apr. 5, 2004

(65) Prior Publication Data

US 2005/0221490 A1 Oct. 6, 2005

(51) Int. Cl.
*C12Q 1/68* (2006.01)
*C07H 21/04* (2006.01)

(52) U.S. Cl. .............................................. 435/6; 514/44
(58) Field of Classification Search ........................ None
See application file for complete search history.

(56) References Cited

U.S. PATENT DOCUMENTS

| | | | |
|---|---|---|---|
| 2003/0108923 | A1 | 6/2003 | Tuschl et al. |
| 2006/0003322 | A1* | 1/2006 | Bentwich ........................ 435/6 |
| 2007/0031844 | A1* | 2/2007 | Khvorova et al. .............. 435/6 |

FOREIGN PATENT DOCUMENTS

| | | | |
|---|---|---|---|
| WO | WO 01/88124 | * | 5/2001 |
| WO | WO 03/029459 | A2 | 4/2003 |
| WO | WO 2004/007718 | A2 | 1/2004 |
| WO | WO2004/044123 | A2 | 5/2004 |
| WO | WO2004/048511 | A2 | 6/2004 |

OTHER PUBLICATIONS

Wiebusch et al (2004) Journal of General Virology, 85, 179-184.*
Paddison et al (2002) Genes and Development, 16, 948-958.*
Vanitharani et al (2003) PNAS, 100, 16, 9632-9636.*
Pfitzner et al (1987) Journal of Virology, 61, 9, 2902-2909.*
Taliansky et al (2003) 77, 5, 3031-3040.*
Amarzguioui, Mohammed, et al., "Tolerance for mutations and chemical modifications in a siRNA", *Nucleic Acids Research* 2003, 31(2):589-595.
Bartel, David P., "MicroRNAs: Genomics, Biogenesis, Mechanism, and Function", *Cell* 2004, 116:281-297.
Beigelman, Leonid, et al.. "Chemical Modification of Hammerhead Ribozymes", *The Journal of Biological Chemistry* 1995, 270(43):25702-25708.
Elbashir, Sayda M., et al., "Duplexes of 21-nucleotide RNAs mediate RNA interference in cultured mammalian cells", *Nature* 2001, 411:494-498.
Holen, Torgeir, et al., "Positional effects of short interfering RNAs targeting the human coagulation trigger Tissue Factor", *Nucleic Acids Research* 2002, 30(8):1757-1766.
Holen, Torgeir, et al., "Similar behaviour of single-strand and double-strand siRNAs suggests they act through a common RNAi pathway", *Nucleic Acids Research* 2003, 31(9):2401-2407.
Howard, Ken, "Unlocking the money-making potential of RNAi", *Nature Biotechnology* 2003, 21(12):1441-1446.
Kurreck, Jens, "Antisense technologies Improvement through novel chemical modifications", *Eur. J. Biochem.* 2003, 270:1628-1644.
Meister, Gunter, et al., "Sequence-specific inhibition of microRNA- and siRNA-induced RNA silencing", *RNA* 2004, 10:544-550.
Nelson, Peter, et al., "The microRNA world: small is mighty", *Trends in Biochemical Sciences* 2003, 28(10):534-540.
Berezikov et al., "Phylogenetic Shadowing and Computational Identification of Human MicroRNA Genes", Cell, vol. 120, pp. 21-24 (2005).
Seitz, et al., "A Large Imprinted MicroRNA Gene Cluster at the Mouse Elkl-Gtl2 Domain", Genome Research, pp. 2. 1-8 (2004).
Xie et al., "Systematic Discovery of Regulatory Motifs in Human Promoters and 3' UTR's by Comparison of Several Mammals", Nature, pp. 1-8 (2005).
Office Action mailed May 09, 2008 for U.S. Appl. No. 10/968,821 filed Oct. 19, 2004.

\* cited by examiner

*Primary Examiner*—Bruce Campell
*Assistant Examiner*—Michelle Horning
(74) *Attorney, Agent, or Firm*—Hoffman & Baron, LLP; Irving N. Feit

(57) ABSTRACT

The invention relates to isolated nucleic acid molecules comprising the sequence of a DNA virus microRNA. In another embodiment, the invention relates to single stranded DNA virus microRNA molecules. In yet another embodiment, the invention relates to single stranded anti-DNA virus microRNA molecules.

37 Claims, 4 Drawing Sheets

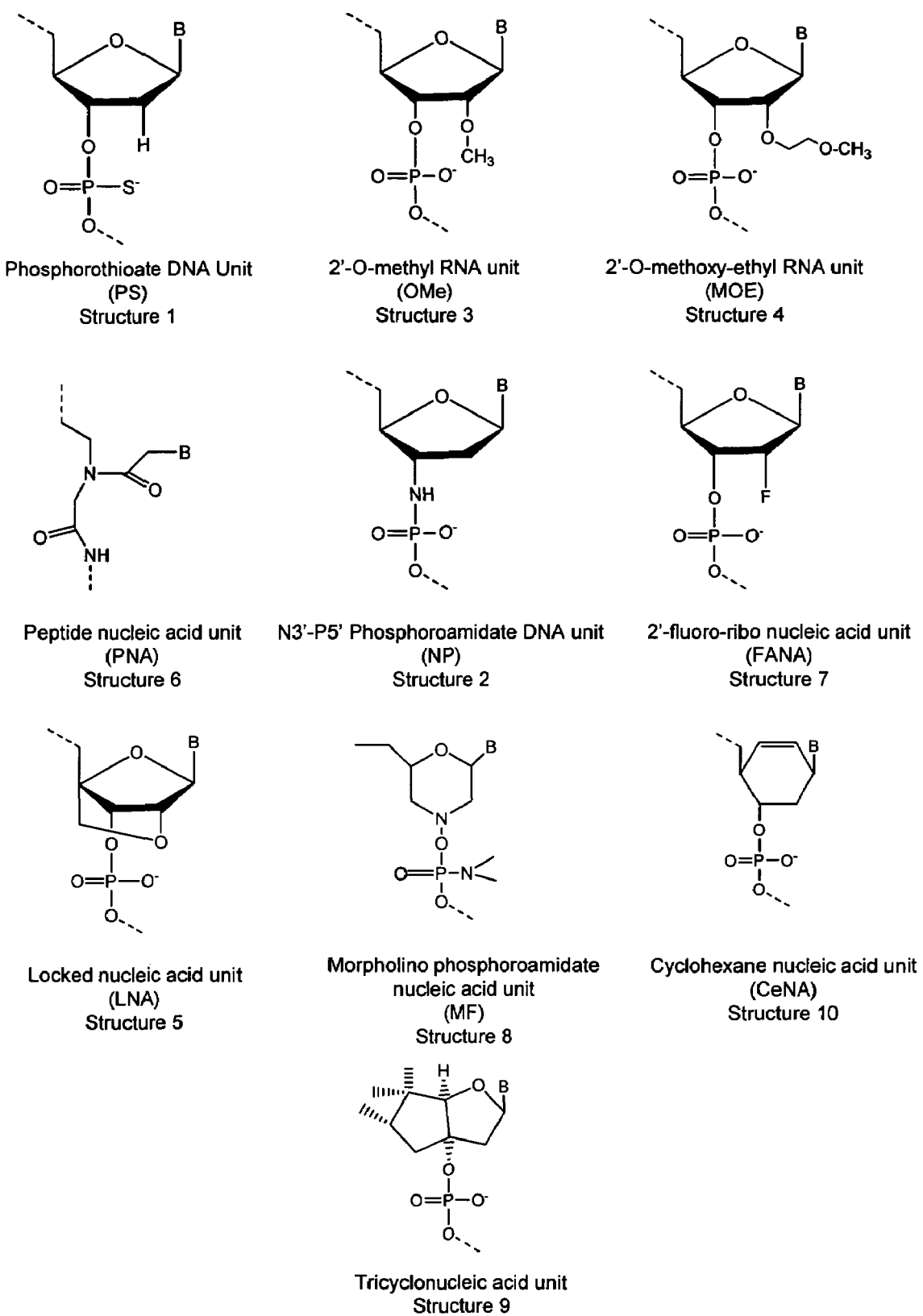

Figures 2A and B
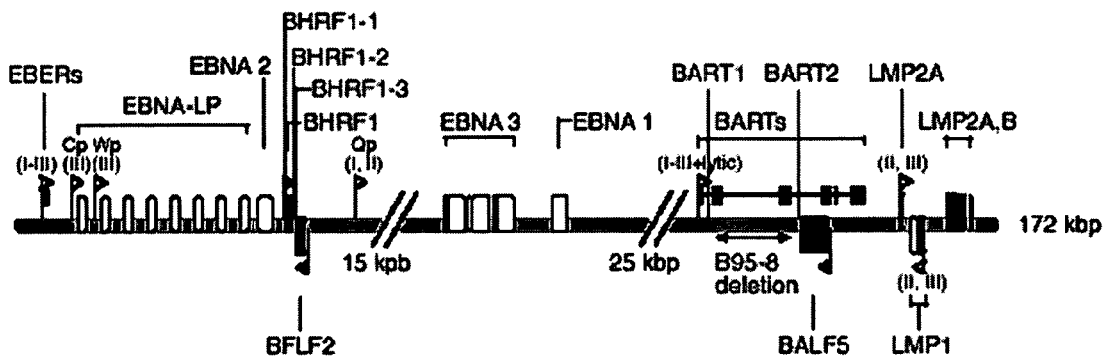

Figures 2C and D
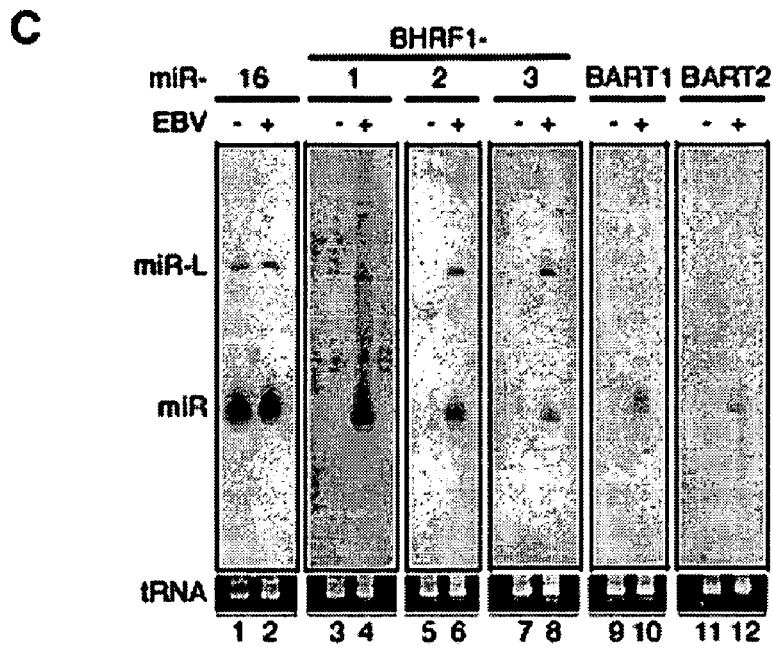
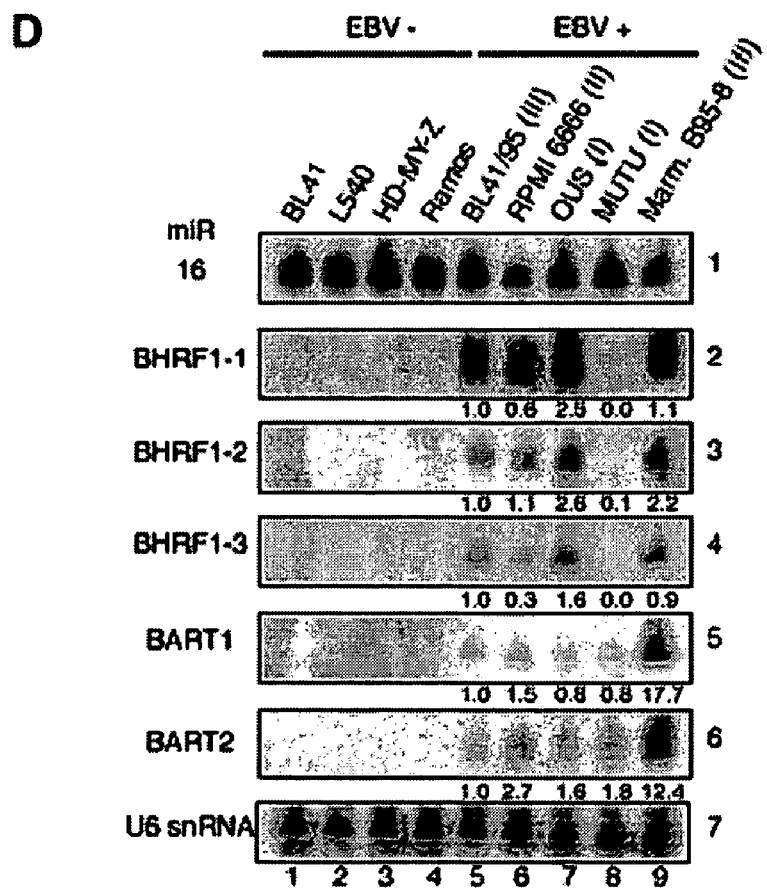

DNA VIRUS MICRORNA

BACKGROUND OF THE INVENTION

MicroRNAs are small RNA molecules of about 22 nucleotides. These microRNA molecules can control gene expression in a sequence specific manner in a wide variety of organisms.

In many organisms, RNA silencing mediated by double-stranded RNA (dsRNA), such as siRNA and microRNA, is part of an innate immune response against RNA viruses and transposable elements. Counter defense strategies to thwart the host response were found in, for example, plant viruses and the insect Flock House virus. These viruses express inhibitors, e.g., dsRNA-binding proteins, that interfere with the host cell RNA silencing machinery.

For example, microRNAs are reported to block translation after partially hybridizing to the non-coding 3' region of mRNAs of target genes. The genes targeted by microRNAs largely remain to be characterized. However, there is growing evidence that microRNAs are implicated in various diseases and illnesses. For instance, drosophila microRNAs have been shown to target genes involved in apoptosis, and B-cell chronic lymphocytic leukemia has been linked to the deletion of two microRNAs.

However, to date, the existence of microRNA encoded by mammalian viruses have not been reported. Identifying mammalian virus microRNAs, and, if they exist, understanding their biological function would facilitate the development of new anti-viral drugs.

Therefore, there is a need to identify viral microRNAs, and for new materials and methods that can help elucidate the function of known and future virus microRNAs.

Due to the ability of microRNAs to induce RNA degradation or repress translation of mRNA which encode important proteins, there is also a need for novel molecules that inhibit DNA virus microRNA-induced cleavage or translation repression of target mRNAs.

SUMMARY THE INVENTION

In one embodiment, the invention relates to an isolated nucleic acid molecule comprising the sequence of a DNA virus microRNA.

In another embodiment, the invention relates to an isolated single stranded DNA virus microRNA molecule. The molecule comprises a minimum of ten moieties and a maximum of fifty moieties on a molecular backbone, the molecular backbone comprising backbone units. Each moiety comprises a base bonded to a backbone unit wherein at least ten contiguous bases have the same sequence as a sequence of bases in a DNA virus microRNA molecule, except that up to thirty percent of the bases pairs may be wobble base pairs, and up to 10% of the contiguous bases are additions, deletions, mismatches, or combinations thereof; and no more than fifty percent of the contiguous moieties contain deoxyribonucleotide backbone units.

In a further embodiment, the invention relates to an isolated single stranded anti-DNA virus microRNA molecule. The anti-DNA virus microRNA molecule comprises a minimum of ten moieties and a maximum of fifty moieties on a molecular backbone, the molecular backbone comprising backbone units. Each moiety comprising a base bonded to a backbone unit, each base forming a Watson-Crick base pair with a complementary base wherein at least ten contiguous bases have a sequence complementary to a contiguous sequence of bases in a DNA virus microRNA molecule, except that up to thirty percent of the bases pairs may be wobble base pairs, and up to 10% of the contiguous bases are additions, deletions, mismatches, or combinations thereof, no more than fifty percent of the contiguous moieties contain deoxyribonucleotide backbone units; and the molecule is capable of inhibiting microRNP activity.

In yet a further embodiment, the invention relates to a method for inhibiting microRNP activity in a cell. The microRNP comprises a DNA virus microRNA molecule, the DNA virus microRNA molecule comprising a sequences of bases complementary to the sequence of bases in a single stranded anti-DNA virus microRNA molecule. The method comprises introducing into the cell a single-stranded anti-DNA virus microRNA molecule comprising a sequence of a minimum of ten moieties and a maximum of fifty moieties on a molecular backbone, the molecular backbone comprising backbone units, each moiety comprising a base bonded to a backbone unit, each base forming a Watson-Crick base pair with a complementary base, wherein at least ten contiguous bases of the anti-DNA virus microRNA molecule are complementary to the DNA virus microRNA, except that up to thirty percent of the bases may be substituted by wobble base pairs, and up to ten percent of the at least ten moieties are addition, deletions, mismatches, or combinations thereof; and no more than fifty percent of the contiguous moieties contain deoxyribonuleotide backbone units.

In yet another embodiment, the invention relates to a method for treating a DNA virus infection in a mammal in need thereof. The method comprises introducing into the mammal an anti-DNA virus microRNA molecule.

In another embodiment, the invention relates to an isolated microRNP comprising an isolated nucleic acid molecule described herein.

In a further embodiment, the invention relates to an isolated microRNP comprising an isolated single stranded DNA virus microRNA molecule.

DESCRIPTION OF THE FIGURES

FIG. 1 shows the modified nucleotide units discussed in the specification. B denotes any one of the following nucleic acid bases: adenosine, cytidine, guanosine, thymine, or uridine.

FIG. 2. EBV expresses microRNAs. (A) Diagram of the microRNA containing segments of the EBV genome. Latent genes are indicated with white boxes, lytic genes with black boxes, previously known non-coding RNAs with blue and newly identified microRNAs with red. Promoters active at latent stages (I, II, or III) are illustrated as white pennants, those active at lytic stage as black pennants, and those active at all stages as gray pennants. The intronic segments within the BARTs region are indicated as dashed lines, the exonic segments with bold bars. (B) Predicted fold-back precursors of the EBV microRNAs. The mature microRNA is highlighted in red. An asterisk is used to denote a low abundant small RNA that was cloned from the strand opposite to the microRNA-BHRF1-2 strand. (C) Northern blots for EBV microRNAs using total RNA isolated from uninfected BL-41 (−) and EBV-infected BL41/95 (+) cells. The expression of human miR-16 (Table S1) was also examined for reference. The position of migration of the mature microRNAs (miR) and its fold-back precursors (miR-L) are indicated. Equal loading of the gel before transfer to the membrane was monitored by ethidium bromide staining of the tRNA band. (D) Northern blots for EBV microRNAs using total RNA isolated from various Hodgkin and Burkitt lymphoma cell lines. The latency stage for EBV positive lines is indicated in parentheses. The numbers below the miR signals indicate relative signal intensity with respect to BL41/95 signals after normalizing for gel loading using the U6 snRNA signal.

DETAILED DESCRIPTION OF THE INVENTION

Figure 3:
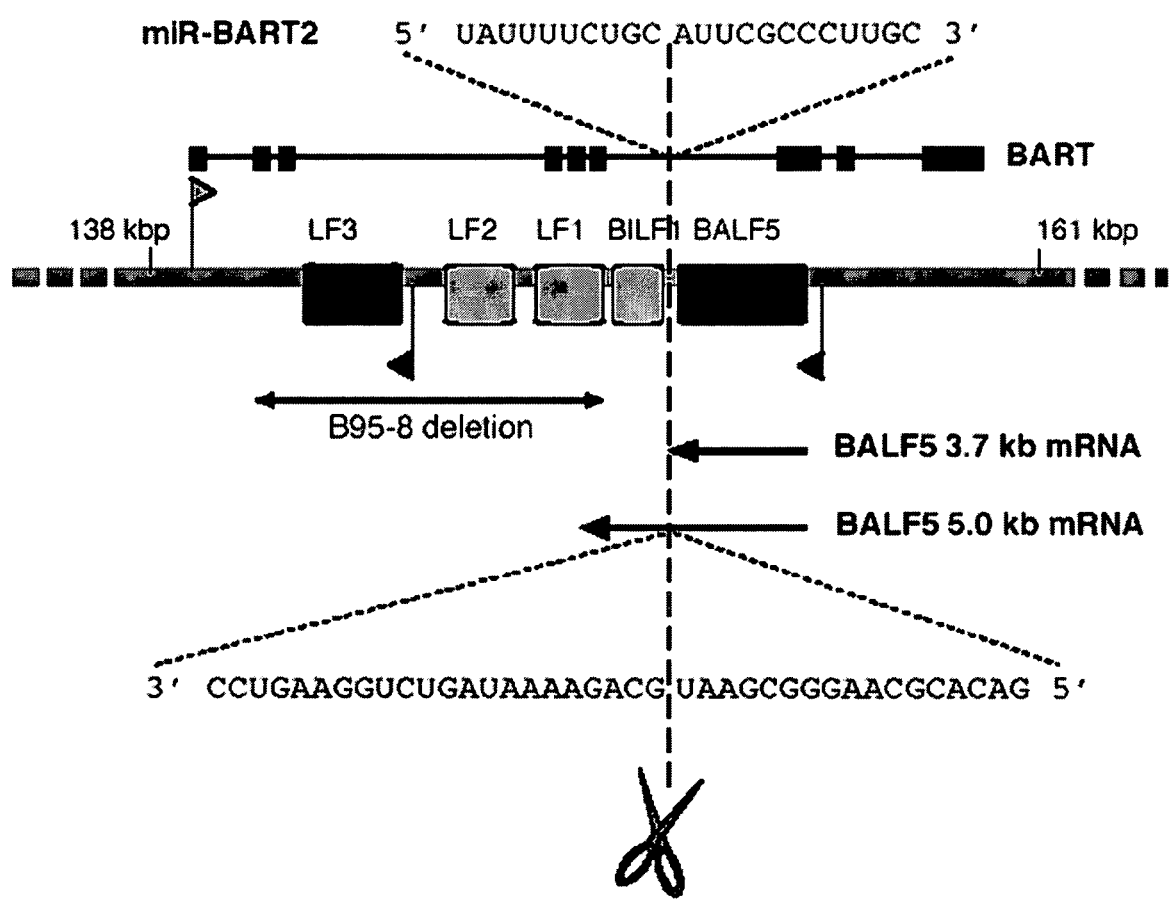
FIG. 3. Schematic representation of miR-BART2-guided cleavage of BALF5 mRNA. Lytic genes are shown as black boxes and genes for which the expression has not been characterized are indicated in gray (GenBank entry V01555). The miR-BART2 sequence is aligned relative to the nucleotide sequence and the processing site of the BALF5 mRNA. The prediction position of BALF5 mRNA cleavage coincides with the mapped terminus of the 3.7 kb processed form.

The inventors have discovered DNA virus-encoded microRNAs. Thus, the invention relates to an isolated single stranded DNA virus microRNA molecule.

MicroRNA molecules are known in the art (see, for example, Bartel, *Cell*, 2004, 116, 281-297 for a review on microRNA molecules). The article by Bartel is hereby incorporated by reference. Such molecules are derived from genomic loci and are produced from specific microRNA genes.

Mature microRNA molecules are processed from precursor transcripts that form local hairpin structures. The hairpin structures are typically cleaved by an enzyme known as Dicer, generating thereby one microRNA duplex. See the above reference by Bartel.

Usually, one of the two strands of a microRNA duplex is packaged in a microRNA ribonucleoprotein complex (microRNP). A microRNP in, for example, humans, also includes the proteins eIF2C2, the helicase Gemin3, and Gemin 4.

In one embodiment, the invention relates to an isolated nucleic acid molecule comprising a DNA virus microRNA sequence or a DNA virus hairpin precursor sequence which contains a DNA virus microRNA. "Isolated" as used herein is defined below. The sequence of the DNA virus microRNA can be a DNA or RNA molecule.

In addition to the sequence of the DNA virus microRNA or hairpin precursor, the nucleic acid molecule may also have one or more additional nucleotides. Any nucleotide can be added. There is no upper limit to the additional number of nucleotides. Typically, no more than about 500 nucleotides, and preferably no more than about 300 nucleotides are added to the DNA virus microRNA sequence or hairpin precursor sequence. In one embodiment, the DNA virus microRNA is part of a hairpin precursor sequence of fragment thereof.

The DNA virus microRNA can, for example, be inserted into a vector, such as, for example, a recombinant vector. Typically, to construct such a recombinant vector containing a DNA virus microRNA, the hairpin precursor sequence which contains the DNA virus microRNA sequence, is incorporated into the vector. See for example, Chen et al. *Science* 2004, 303:83-86.

The recombinant vector may be any recombinant vector, such as a plasmid, a cosmid or a phage. Recombinant vectors generally have an origin of replication. The vector may be, for example, a viral vector, such as an adenovirus vector or an adeno-associated virus (AAV) vector. See for example: Ledley 1996, *Pharmaceutical Research* 13:1595-1614 and Verma et al. *Nature* 1997, 387:239-242.

The vector may further include a selectable marker, such as for instance a drug resistance marker or a detectable gene marker, such as β-galactosidase.

In a preferred embodiment, the nucleic acid molecule consists essentially of a DNA virus microRNA sequence or a hairpin precursor sequence. In another preferred embodiment, the nucleic acid molecule consists essentially of any one of the DNA virus microRNA sequence or hairpin precursor sequence shown in Table A.

The DNA virus can be any DNA virus known to those skilled in the art. Preferably, the DNA virus infects mammalian cells. Examples of mammals include laboratory animals, such as dogs and cats, farm animals, such as cows, horses and sheeps, laboratory animals, such as rats, mice and rabbits, and primates, such as monkeys and humans.

The DNA virus can be a single stranded or double stranded DNA virus. Examples of single stranded and double stranded DNA viruses are listed in the Table B.

Preferably, the DNA virus is Epstein barr virus (EBV). Examples of EBV microRNAs and the corresponding hairpin precursor sequences are shown in Table A.

TABLE A

EBV microRNA and Hairpin Precursor Sequences

| Virus | microRNA Sequence 5' → 3' | Hairpin Precursor microRNA Sequence* (5' → 3') |
|---|---|---|
| EBV | UAACCUGAUCAGCCCCGGAGUU (SEQ. ID. NO. 1) | UAUUAACCUGAUCAGCCCCGGAGUUGCCUGUUUCAU CACUAACCCCGGGCCUGAAGAGGUUGACAA (SEQ. ID. NO. 6) |
| | UAUCUUUUGCGGCAGAAAUGAA (SEQ. ID. NO. 2) | CUUUAAAUUCUGUUGCAGCAGAUAGCUGAUACCCA AUGUUAUCUUUUGCGGCAGAAAUUGAAAG (SEQ. ID. NO. 7) |
| | UAACGGGAAGUGUGUAAGCACAC (SEQ. ID. NO. 3) | UCUAACGGGAAGUGUGUAAGCACACACGUAAUUUGC AAGCGGUGCUUCACGCUCUUCGUUAAAAU (SEQ. ID. NO. 8) |
| | UCUUAGUGGAAGUGACGUGCU (SEQ. ID. NO. 4) | CGGGGUCUUAGUGGAAGUGACGUGCUGUGAAUACAG GUCCAUAGCACCGCUAUCCACUAUGUCUCGCCCG (SEQ. ID. NO. 9) |
| | UAUUUUCUGCAUUCGCCCUUGC (SEQ. ID. NO. 5) | ACUAUUUUCUGCAUUCGCCCUUGCGUGUCCAUUGUU GCAAGGAGCGAUUUGGAGAAAAUAAA (SEQ. ID. NO. 10) |

TABLE A-continued

EBV microRNA and Hairpin Precursor Sequences

| Virus | microRNA Sequence 5' → 3' | Hairpin Precursor microRNA Sequence* (5' → 3') |
|---|---|---|

*In bold, mature microRNA sequence. In italics, a low abundant sequence corresponding to the non-functional strand of the microRNA

TABLE B

Single Stranded and Double Stranded DNA Viruses

| Family | Subfamily | Genus | Type species |
|---|---|---|---|
| The dsDNA Viruses | | | |
| Poxviridae | | | |
| | Chordopoxvirinae | | |
| | | Orthopoxvirus | Vaccinia virus |
| | | Parapoxvirus | Orf virus |
| | | Leporipoxvirus | Myxoma virus |
| | | Molluscipoxvirus | Molluscum contagiosum virus |
| Herpesviridae | | | |
| | Alphaherpesvirinae | | |
| | | Simplexvirus | Human herpesvirus 1 |
| | | Varicellovirus | Human herpesvirus 3 |
| | Betaherpesvirinae | | |
| | | Cytomegalovirus | Human herpesvirus 5 |
| | | Muromegalovirus | Murid herpesvirus 1 |
| | | Roseolovirus | Human herpesvirus 6 |
| | Gammaherpesvirinae | | |
| | | Lymphocryptovirus | Human herpesvirus 4 (EBV) |
| | | Rhadinovirus | Saimiriine herpesvirus 2 |
| Adenoviridae | | | |
| | | Mastadenovirus | Human adenovirus C |
| Polyomaviridae | | | |
| | | Polyomavirus | Simian virus 40 |
| Papillomaviridae | | | |
| | | Papillomavirus | Cottontail rabbit papillomavirus |
| The ssDNA Viruses | | | |
| Parvoviridae | | | |
| | Parvovirinae | | |
| | | Parvovirus | Mice minute virus |
| | | Erythrovirus | B19 virus |
| | | Dependovirus | Adeno-associated virus 2 |

In another embodiment, the invention relates to analogs of DNA virus microRNAs or hairpin precursors described above, including those having the sequences shown in Table A. In this embodiment, the DNA virus microRNA molecule comprises a minimum number of ten moieties, preferably a minimum of thirteen, more preferably a minimum of fifteen, even more preferably a minimum of 18, and most preferably a minimum of 21 moieties.

The DNA virus microRNA molecule comprises a maximum number of fifty moieties, preferably a maximum of forty, more preferably a maximum of thirty, even more preferably a maximum of twenty-five, and most preferably a maximum of twenty-three moieties. A suitable range of minimum and maximum numbers of moieties may be obtained by combining any of the above minima with any of the above maxima.

Each moiety comprises a base bonded to a backbone unit. In this specification, a base refers to any one of the nucleic acid bases present in DNA or RNA. The base can be a purine or pyrimidine. Examples of purine bases include adenine (A) and guanine (G). Examples of pyrimidine bases include thymine (T), cytosine (C) and uracil (U). Each base of the moiety forms a Watson-Crick base pair with a complementary base.

Watson-Crick base pairs as used herein refer to the hydrogen bonding interaction between, for example, the following bases: adenine and thymine (A-T); adenine and uracil (A-U); and cytosine and guanine (C-G). The adenine can be replaced with 2,6-diaminopurine without compromising base-pairing.

The backbone unit may be any molecular unit that is able to stably bind to a base and to form an oligomeric chain. Suitable backbone units are well known to those in the art.

For example, suitable backbone units include sugar-phosphate groups, such as the sugar-phosphate groups present in ribonucleotides, deoxyribonucleotides, phosphorothioate deoxyribose groups, N'3-N'5 phosphoroamidate deoxyribose groups, 2'O-alkyl-ribose phosphate groups, 2'-O-alkyl-alkoxy ribose phosphate groups, ribose phosphate group containing a methylene bridge, 2'-fluororibose phosphate groups, morpholino phosphoroamidate groups, cyclohexene groups, tricyclo phosphate groups, and amino acid molecules.

Preferably, the DNA virus microRNA molecule comprises at least one moiety which confers increased nuclease resistance. Such molecules comprise at least one moiety that is not recognized by a nuclease. Therefore, the nuclease resistance of the molecule is increased compared to a sequence containing only unmodified ribonucleotide, unmodified deoxyribonucleotide or both. Such modified moieties are well known in the art, and were reviewed, for example, by Kurreck, Eur. J. Biochem. 270, 1628-1644 (2003).

The nuclease resisted can be an exonuclease, an endonuclease, or both. The exonuclease can be a 3'→5' exonuclease or a 5'→3' exonuclease. Examples of 3'→5' human exonuclease include PNPT1, Werner syndrome helicase, RRP40, RRP41, RRP42, RRP45, and RRP46. Examples of 5'→3' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

A modified moiety can occur at any position in the DNA virus microRNA molecule. For example, to protect the DNA virus microRNA molecule against 3'→5' exonucleases, the molecule can have at least one modified moiety at the 3' end of the molecule and preferably at least two modified moieties at the 3' end. If it is desirable to protect the molecule against 5'→3' exonuclease, the DNA virus microRNA molecule can have at least one modified moiety and preferably at least two modified moieties at the 5' end of the molecule. The DNA virus microRNA molecule can also have at least one and preferably at least two modified moieties between the 5' and 3' end of the molecule to increase resistance of the molecule to endonucleases. Preferably, at least about 10%, more preferably at least about 25%, even more preferably at least about 50%, and further more preferably at least about 75%, and most preferably about 95% of the moieties are modified. In one embodiment, all of the moieties are nuclease resistant.

In another embodiment, the DNA virus microRNA molecule comprises at least one modified deoxyribonucleotide moiety. Suitable modified deoxyribonucleotide moieties are known in the art.

A suitable example of a modified deoxyribonucleotide moiety is a phosphorothioate deoxyribonucleotide moiety. See structure 1 in FIG. 1. A DNA virus microRNA molecule comprising phosphorothioate deoxyribonucleotide moieties is generally referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety. See structure 2 in FIG. 1. An oligonucleotide molecule comprising phosphoroamidate deoxyribonucleotide moieties is generally referred to as phosphoroamidate (NP) DNA. See, for example, Gryaznov et al., J. Am. Chem. Soc. 116, 3143-3144 (1994).

In another embodiment, the molecule comprises at least one modified ribonucleotide moiety. Suitable modified ribonucleotide moieties are known in the art.

A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. See structure 3 in FIG. 1. An oligoribonucleotide molecule comprising ribonucleotide moieties substituted at the 2' position with a $C_1$ to $C_4$ alkyl group is generally referred to as a 2'-O-($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy (alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. See structure 4 in FIG. 1. An oligonucleotide molecule comprising more than one ribonucleotide moiety that is substituted at the 2' position with a C1 to $C_4$ alkoxy-$C_1$ to $C_4$ alkyl group is referred to as a 2'-O-($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. See structure 5 in FIG. 1. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Ørum et al., Curr. Opinion Mol. Ther. 3, 239-243 (2001); Koshkin et al., Tetrahedron 54, 3607-3630 (1998); Obika et al., Tetrahedron Lett. 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. Such 2'-fluororibonucleotide moieties are known in the art. Molecules comprising 2'-fluororibonucleotide moieties are generally referred to herein as 2'-fluororibo nucleic acids (FANA). See structure 7 in FIG. 1. Damha et al., J. Am. Chem. Soc. 120, 12976-12977 (1998).

In another embodiment, the DNA virus microRNA molecule comprises at least one base bonded to an amino acid residue. Moieties that have at least one base bonded to an amino acid residue will be referred to herein as peptide nucleic acid (PNA) moieties. Such moieties are nuclease resistance, and are known in the art. Molecules having PNA moieties are generally referred to as peptide nucleic acids. See structure 6 in FIG. 1. Nielson, Methods Enzymol. 313, 156-164 (1999); Elayadi, et al, id.; Braasch et al., Biochemistry 41, 4503-4509 (2002), Nielsen et al., Science 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta-, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications*, Horizon Scientific Press, pages 1-19; Nielsen et al., *Science* 254: 1497-1500.) One example of an amino acid residue of a PNA moiety is N-(2-aminoethyl)-glycine.

Further examples of PNA moieties include cyclohexyl PNA, retro-inverso PNA, phosphone PNA, propionyl PNA and aminoproline PNA. For a description of these PNA moieties, see FIG. 5 of Nielsen et al., *Peptide Nucleic Acids-Protocols and Applications*, Horizon Scientific Press, pages 1-19. FIG. 5 on page 7 of Nielsen et al. is hereby incorporated by reference.

PNA can be chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability.

Peptide nucleic acids are also commercially available from Applied Biosystems (Foster City, Calif., USA).

Additional nuclease resistant moieties are known in the art. For example, the DNA virus microRNA molecule comprises at least one morpholino phosphoroamidate nucleotide moiety. Molecules comprising morpholino phosphoroamidate nucleotide moieties are generally referred to as morpholino (MF) nucleic acids. See structure 8 in FIG. 1. Heasman, Dev. Biol. 243, 209-214 (2002). Morpholino oligonucleotides are commercially available from Gene Tools LLC (Corvallis, Oreg., USA).

In another example of a nuclease resistant moiety, the DNA virus microRNA molecule comprises at least one cyclohexene nucleotide moiety. Molecules comprising cyclohexene nucleotide moieties are generally referred to as cyclohexene nucleic acids (CeNA). See structure 10 in FIG. 1. Wang et al., J. Am. Chem. Soc. 122, 8595-8602 (2000), Verbeure et al., Nucleic Acids Res. 29, 4941-4947 (2001).

In a final example of a nuclease resistant moiety, the DNA virus microRNA molecule comprises at least one tricyclo nucleotide moiety. Molecules comprising tricyclo nucleotide moieties are generally referred to as tricyclo nucleic acids (tcDNA). See structure 9 in FIG. 1. Steffens et al., J. Am. Chem. Soc. 119, 11548-11549 (1997), Renneberg et al., J. Am. Chem. Soc. 124, 5993-6002 (2002).

In another embodiment, inverted nucleotide caps can be attached to the 5' end, the 3' end, or both ends of the molecule in order to increase nuclease resistance of the DNA virus microRNA molecules of the present invention to exonucleases. An inverted nucleotide cap refers to a 3'→5' sequence of nucleic acids attached to the DNA virus microRNA molecule at the 5' and/or the 3' end. There is no limit to the maximum number of nucleotides in the inverted cap just as long as it does not interfere with binding of the DNA virus microRNA molecule to its target mRNA. Any nucleotide can be used in the inverted nucleotide cap. Usually, the nucleotide cap is less than about forty nucleotides in length, preferably less than about thirty nucleotides in length, more preferably less than about twenty nucleotides in length, and even more preferably less than about ten nucleotides in length. Typically, the inverted nucleotide cap is one nucleotide in length. The nucleotide for the inverted cap is generally thymine, but can be any nucleotide such as adenine, guanine, uracil, or cytosine.

Alternatively, a chemical cap can be attached to the 5' end, to the 3' end, to both ends of the molecule, and/or to any moiety(ies) between the 5' end and 3' end of the DNA virus microRNA molecule in order to increase nuclease resistance to exonucleases and/or endonucleases. The chemical cap can be any chemical group known to those in the art for increasing nuclease resistance of nucleic acids. Example of such chemical caps include alkyl hydroxides or alkyl amines. Alkyl hydroxides are sometimes referred to as alkyl glycols (e.g., ethylene glycol). Alkyl amines are sometimes referred to as amino linkers.

The alkyl chain can be straight chain or branched. The minimum number of carbon atoms present in the alkyl chain is one, preferably at least two, and more preferably at least about three carbon atoms. The maximum number of carbon atoms present in the alkyl chain is about eighteen, preferably about sixteen, and more preferably about twelve. Typically alkyl groups include methyl, ethyl, and propyl. The alkyl groups can be further substituted with one or more hydroxyl and/or amino groups.

Some examples of amino linkers are shown in Table C. The amino linkers listed in Table C lists are commercially available from TriLink Biotechnologies, San Diego, Calif.

TABLE C

| Amino Linkers from TriLink Biotechnologies |
| --- |
| 2'-Deoxycytidine-5-C6 Amino Linker (3' Terminus) |
| 2'-Deoxycytidine-5-C6 Amino Linker (5' or Internal) |
| 3' C3 Amino Linker |
| 3' C6 Amino Linker |
| 3' C7 Amino Linker |
| 5' C12 Amino Linker |
| 5' C3 Amino Linker |
| 5' C6 Amino Linker |
| C7 Internal Amino Linker |
| Thymidine-5-C2 Amino Linker (5' or Internal) |
| Thymidine-5-C6 Amino Linker (3' Terminus) |
| Thymidine-5-C6 Amino Linker (Internal) |

Chimeric DNA virus microRNA molecules containing a mixture of any of the moieties mentioned above are also known, and may be made by methods known, in the art. See, for example, references cited above, and Wang et al, Proc. Natl. Acad. Sci. USA 96, 13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

The DNA virus microRNA molecules of the invention comprise at least ten, preferably at least thirteen, more preferably at least fifteen, and even more preferably at least twenty contiguous bases having the sequence of a naturally occurring DNA virus microRNA molecule. In a preferred embodiment, the DNA virus microRNA molecules comprise the entire sequence of a DNA virus microRNA molecule, such as any one of the DNA virus microRNA molecule sequences shown in Table A.

The remaining bases in the molecule, if any, can be any modified or unmodified moiety described above. In one embodiment, the DNA virus microRNA molecule comprises at least one moiety which is a ribonucleotide moiety or a deoxyribonucleotide moiety.

Any number of additional moieties, up to a maximum of forty moieties, having any base sequence can be added to the moieties comprising the contiguous base sequence, as long as the total number of moieties in the molecule does not exceed fifty. The additional moieties can be added to the 5' end, the 3' end, or to both ends of the contiguous sequence. The additional bases can include a sequence of bases at the 5' end and/or a sequence of bases at the 3' end present in the hairpin precursor from which the DNA virus microRNA is derived or any fragment thereof. In one embodiment, the hairpin precursor sequence is any one of the hairpin precursor sequences shown in Table A.

For the contiguous bases mentioned above, up to thirty percent of the base pairs may be substituted by wobble base pairs. As used herein, wobble base pairs refer to either: i) substitution of a cytosine with a uracil, or 2) the substitution of an adenine with a guanine, in the sequence of the DNA virus microRNA molecule. These wobble base pairs are generally referred to as UG or GU wobbles. Table D shows the number of contiguous bases and the maximum number of wobble base pairs in the DNA virus microRNA molecule.

TABLE D

Number of contiguous Bases and
Maximum Number of Wobble Bases

| | No. of Contiguous Bases | | | | | | | | |
|---|---|---|---|---|---|---|---|---|---|
| | 10 | 11 | 12 | 13 | 14 | 15 | 16 | 17 | 18 |
| Max. No. of Wobble Base Pairs | 3 | 3 | 3 | 3 | 4 | 4 | 4 | 5 | 5 |

| | No. of Contiguous Bases | | | | |
|---|---|---|---|---|---|
| | 19 | 20 | 21 | 22 | 23 |
| Max. No. of Wobble Base Pairs | 5 | 6 | 6 | 6 | 6 |

Further, in addition to the wobble base pairs, up to ten percent, and preferably up to five percent of the contiguous bases can be additions, deletions, mismatches or combinations thereof. Additions refer to the insertion in the contiguous sequence of any moiety described above comprising any one of the bases described above. Deletions refer to the removal of any moiety present in the contiguous sequence. Mismatches refer to the substitution of one of the moieties comprising a base in the contiguous sequence with any of the above described moieties comprising a different base.

The additions, deletions or mismatches can occur anywhere in the contiguous sequence, for example, at either end of the contiguous sequence or within the contiguous sequence of the DNA virus microRNA molecule. Typically, the additions, deletions or mismatches occur at the end of the contiguous sequence if the contiguous sequence is relatively short, such as, for example, from about ten to about fifteen moieties in length. If the contiguous sequence is relatively long, such as, for example, a minimum of sixteen contiguous sequences, the additions, deletions, or mismatches typically occur anywhere in the contiguous sequence.

For example, none or one of the contiguous bases may be additions, deletions, or mismatches when the number of contiguous bases is ten to nineteen; and a maximum of one or two additions, deletions, or mismatches are permissible when the number of contiguous bases is twenty to twenty-three.

Furthermore, no more than fifty percent, and preferably no more than thirty percent, of the contiguous moieties contain deoxyribonucleotide backbone units. Table E and F show the number of contiguous bases and the maximum number of deoxyribonucleotide backbone units.

TABLE E

Fifty Percent of the Contiguous Moieties containing
Deoxyribonucleotide Backbone Units

| | No. of Contiguous Bases | | | | | | | | |
|---|---|---|---|---|---|---|---|---|---|
| | 10 | 11 | 12 | 13 | 14 | 15 | 16 | 17 | 18 |
| Max. No. of Deoxyribonucleotide Backbone Units | 5 | 5 | 6 | 6 | 7 | 7 | 8 | 8 | 9 |

| | No. of Contiguous Bases | | | | |
|---|---|---|---|---|---|
| | 19 | 20 | 21 | 22 | 23 |
| Max. No. of Deoxyribonucleotide Backbone Units | 9 | 10 | 10 | 11 | 11 |

TABLE F

Thirty Percent of the Contiguous Moieties Containing
Deoxyribonucleotide Backbone Units

| | No. of Contiguous Bases | | | | | | | | |
|---|---|---|---|---|---|---|---|---|---|
| | 10 | 11 | 12 | 13 | 14 | 15 | 16 | 17 | 18 |
| Max. No. of Deoxyribonucleotide Backbone Units | 3 | 3 | 3 | 3 | 4 | 4 | 4 | 5 | 5 |

| | No. of Contiguous Bases | | | | |
|---|---|---|---|---|---|
| | 19 | 20 | 21 | 22 | 23 |
| Max. No. of Deoxyribonucleotide Backbone Units | 5 | 6 | 6 | 6 | 6 |

In another embodiment, in addition to the wobble base pairs and the further additions, deletions, and mismatches, described above, the moiety corresponding to position 11 in a naturally occurring DNA virus microRNA sequence can be an addition, deletion or mismatch.

The DNA virus microRNA molecule is preferably isolated, which means that it is essentially free of other nucleic acids. Essentially free from other nucleic acids means that the DNA virus microRNA molecule is at least about 90%, preferably at least about 95% and, more preferably at least about 98% free of other nucleic acids.

Preferably, the molecule is essentially pure, which means that the molecules is free not only of other nucleic acids, but also of other materials used in the synthesis and isolation of the molecule. Materials used in synthesis include, for example, enzymes. Materials used in isolation include, for example, gels, such as SDS-PAGE. The molecule is at least about 90% free, preferably at least about 95% free and, more preferably at least about 98% free of such materials.

In another aspect, the invention provides an isolated microRNP comprising any of the isolated nucleic acid sequences described above or analogs of the DNA virus microRNAs or hairpin precursors described above.

In another aspect, the invention provides an anti-DNA virus microRNA molecule. The anti-DNA virus microRNA molecule may be any of the isolated nucleic acid sequences described above or analogs of the DNA virus microRNAs or hairpin precursors described above, except that the sequence of bases of the anti-DNA virus microRNA molecule is complementary to the sequence of bases in a DNA virus microRNA molecule.

Examples of sequences of anti-DNA virus microRNA molecules is shown in Table G.

TABLE G

EBV anti-microRNA Sequences

| Virus | Anti-microRNA Sequence 5' → 3' |
|---|---|
| EBV | AACUCCGGGGCUGAUCAGGUUA (SEQ. ID. NO. 11) |
|  | UUCAAUUCUGCCGCAAAAGAUA (SEQ. ID. NO. 12) |
|  | GUGUGCUUACACACUUCCCGUUA (SEQ. ID. NO. 13) |
|  | AGCACGUCACUUCGACUAAGA (SEQ. ID. NO. 14) |
|  | GCAAGGGCGAAUGCAGAAAAUA (SEQ. ID. NO. 15) |

The anti-DNA virus microRNA molecule can be modified as described above for DNA virus microRNA molecules. In one embodiment, the contiguous moieties in the anti-DNA virus microRNA molecule are complementary to the corresponding DNA virus microRNA molecule. The complementarity of the anti-DNA virus microRNA molecules are subject to the restrictions described above, including to the restriction relating to wobble base pairs, as well as those relating to additions, deletions and mismatches. Preferably, the anti-DNA virus microRNA molecule contains at least one modified moiety if the anti-DNA virus microRNA molecule is perfectly (i.e., 100%) complementary to a DNA virus microRNA molecule.

In another embodiment, the moiety in the anti-DNA virus microRNA molecule at the position corresponding to position 11 of a naturally occurring DNA virus microRNA is non-complementary. The moiety in the anti-DNA virus microRNA molecule corresponding to position 11 of a naturally occurring DNA virus microRNA can be rendered non-complementary by the introduction of an addition, deletion or mismatch, as described above.

Utility

The DNA virus microRNA molecules and anti-DNA virus microRNA molecules of the present invention have numerous in vitro, ex vivo, and in vivo applications.

For example, the microRNA molecules and/or anti-microRNA molecules of the present invention can be introduced into a cell to study the function of the microRNA. Any DNA viral microRNA molecule and/or anti-DNA viral microRNA molecule mentioned above can be introduced into a cell for studying their function.

In one embodiment, a microRNA in a cell is inhibited with a suitable anti-microRNA molecule. Alternatively, the activity of a microRNA molecule in a cell can be can be enhanced by introducing into the cell an additional microRNA molecule. The function of the microRNA can be inferred by observing changes associated with inhibition and/or enhanced activity of the microRNA in the cell.

Thus, in one aspect of the invention, the invention relates to a method for inhibiting microRNP activity in a cell. The microRNP comprises a DNA virus microRNA molecule. The microRNA molecule comprises a sequence of bases complementary to the sequence of bases in a single stranded anti-DNA virus microRNA molecule. Any anti-DNA virus microRNA molecule can be used in the method for inhibiting microRNP activity in a cell, as long as the anti-DNA virus microRNA is complementary, subject to the restrictions described above, to the DNA virus microRNA present in the microRNP.

The anti-DNA virus microRNA molecules of the present invention are capable of inhibiting microRNP activity by binding to the DNA virus microRNA in the microRNP in a host cell. MicroRNP activity refers to the cleavage or the repression of translation of the target sequence. The target sequence may be any sequence which is partially or perfectly complementary to the sequence of bases in a DNA virus microRNA. The target sequence can be, for example, a viral or host messenger RNA.

For example, a DNA virus can produce a microRNA which is complementary to a host derived target sequence that is beneficial to the host cell for defending against the viral infection. The DNA virus microRNA, which is packaged in a microRNP, will inhibit the beneficial effect of the target sequence. Accordingly, the introduction of the anti-DNA virus microRNA molecule inhibits the RNP activity, and thereby reduces harm from the virus.

Alternatively, a host cell can defend against a viral infection by transcribing a gene which is harmful to the virus. For instance, the gene may induce the cell to undergo apoptosis, and therefore the gene is harmful to the virus. A DNA virus microRNA complementary to the target sequence transcribed by the host cell is beneficial to the virus, because the DNA virus micro RNA (in a microRNP) will inhibit the ability of the host cell to undergo apoptosis. Accordingly, the introduction of DNA virus microRNA molecules promotes survival of the cell, thereby enhancing the infection.

The method for inhibiting microRNP activity in a cell comprises introducing into the cell a single-stranded anti-DNA virus microRNA molecule. The anti-DNA virus microRNA molecule can be introduced into a cell by any method described in the art. Some examples are described below.

The cell can be any cell capable of being infected with a particular DNA virus. Particular cells infected by a particular DNA virus are well known to those skilled in the art. For example, it is well known to those in the art that EBV preferentially infects B lymphocytes.

The microRNA molecules or anti-microRNA molecules can be introduced into a cell by any method known to those skilled in the art. For example, the molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule or an anti-microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In *Antisense Technology in the Central Nervous System* (Leslie, R. A., Hunter, A. J. & Robertson, H. A., eds), pp. 147-157, Oxford University Press.

Targeting of a microRNA molecule or an anti-microRNA molecule to a particular cell can be performed by any method known to those skilled in the art. For example, the microRNA molecule or anti-microRNA molecule can be conjugated to an antibody or ligand specifically recognized by receptors on the cell. For example, if the cell is a B lymphocyte, the antibody can be against the cell receptor CD19, CD20, CD21, CD23 or a ligand to these receptors.

In another embodiment, the invention provides a method for treating a DNA virus infection is a mammal in need thereof. The method comprises introducing into the mammal an anti-DNA virus microRNA molecule. The anti-DNA virus microRNA molecules can be introduced into the mammal by any method known to those in the art. For example, the above described methods for introducing the anti-DNA molecules into a cell can also be used for introducing the molecules into a mammal.

EXAMPLES

Example 1

Materials and Methods

Cell lines and viruses. The EBV negative BL-41 and EBV positive BL41/95 cells were described previously (Torsteinsdottir et al., *Int. J. Cancer* 1989, 43:273) and were maintained in RPMI 1640 (Gibco) supplemented with 10% FBS. BL41/95 but not BL-41 contained EBV, as confirmed by Western blot analysis using antibodies against EBNA-1. For analysis of EBV miRNA expression, we also cultured Hodgkin's lymphoma (HD) cells L540 and HD-MY-Z (EBV negative) and RPMI 6666 (EBV positive) and the Burkitt's lymphoma (BL) cells Ramos (EBV negative), Ous and Mutu (EBV positive), and EBV positive Marmoset B95-8 cells that produce infectious B95-8 viral particles. These cell lines were also maintained in RPMI 1640 (Gibco) supplemented with 10% FBS.

RNA preparation, cloning procedure and Northern blot analysis. Total RNA extraction was performed as described previously (Lagos-Quintana et al., *Curr. Biol.* 2002, 12:735). RNA size fractionation and cloning procedure have also been described (14). Northern blot analysis was performed as described (Lagos-Quintana et al., *Curr. Biol.* 2002, 12:735) loading 30 μg of total RNA per lane and using 5' $^{32}$P-radiolableled oligodeoxynucleotides complementary to the miRNA sequence. Equal loading of the gels was confirmed by ethidium bromide staining of the tRNA band or by reprobing the blot for U6 snRNA using $^{32}$P-labeled 5'GCAGGGGC-CATGCTAATCTTCTCTGTATCG (SEQ. ID. NO. 16) oligodeoxynucleotide. Blots were stripped and reprobed several times. Complete stripping of the blot was confirmed by phosphorimaging of the membrane before reprobing.

DNA Sequencing of small RNA cDNA libraries. Bacterial colonies were picked into 96 well plates filled with 20 μl sterile water per well, then diluted 1:1 into a second 96 well plate containing 10 μl PCR cocktail (2 μl 10× Sigma JumpStart PCR buffer, 2 μl 2 mM deoxynucleoside triphosphate mixture, 0.4 μl each 10 μM M13 universal and reverse primers, 0.35 μl 1 U/μl JumpStart REDAccuTaq DNA polymerase (Sigma), and 4.85 μl water. The PCR cycling program consisted of 1'30" at 94° C., followed by 30 cycles of 94° C., 30"; 57° C., 30"; 72° C., 3'30", conditions which largely deplete the primers and deoxynucleotides, obviating the requirement for reaction cleanup prior to sequencing. After diluting the PCR products with 30 μl water, 3 μl was added to wells of a 96 well plate containing 17 μl sequencing cocktail consisting of 1 μl 2.5× BigDye Terminator v3.1 Cycle Sequencing Kit premix, 1.75 μL 5× buffer and 14.25 μl water, and sequencing reactions were carried out for 25 cycles (96° C., 10"; 50° C., 5"; 60° C., 4'). The reaction products were precipitated with 50 μl 100% ethanol/2 μl 3M NaOAc (pH 4.8), pellets were rinsed with 70% ethanol, and after the addition of 10 μl Hi-Di Formamide (Applied Biosystems) and denaturing at 94° C. for 10 min, samples were loaded onto an ABI 3730x1 sequencer.

miRNA target prediction. We first obtained the 3' UTR sequences for 20,153 transcripts in the human genome using Ensmart (Kasprzyk et al., *Genome Res.* 2004, 14:160) as well as the sequences of 175 mature human miRNAs from the RFAM miRNA registry (Griffiths-Jones, *Nucleic Acids Res.*, 2004, 32:D109). miRanda (Enright et al., *Genome Biol.*, 2003, 5:RI, 1) was used to identify miRNA binding sequences in the 3' UTR sequences. The thresholds used for this scan were S:90 and .G: -17 kcal/mol. Targets that were in the 90th percentile of the raw alignment scores were selected as candidate miRNA targets.

Example 2

Identification of EBV Encoded microRNAs

We examined a large DNA virus of the Herpes family, Epstein barr virus (EBV) which preferentially infects human B cells. We cloned the small RNAs from a Burkitt's lymphoma cell line latently infected with EBV. Surprisingly, we found 4% of the cloned small RNAs originated from EBV (Tables 1 and 2). Table 1. Composition of small RNA cDNA libraries prepared from non-infected (−) and DNA virus-infected human cell lines according to sequence annotation. The annotation was based on information from GenBank, a dataset of human tRNA sequences, a dataset of human and mouse sn/snoRNA sequences, a database of microRNAs, predictions of microRNAs (35), and the repeat element annotation of the HG16 human genome assembly from UCSC. The total number of cloned sequences is indicated in parentheses at the bottom line of the table. Sequences that mapped to the human genome allowing up to two mismatches but could not be assigned a specific type were classified as Not annotated; those that did not match to the genome with more than 3 mismatches were classified as Not matched.

| Type | BL-41 Human Cell Line | |
| --- | --- | --- |
| | — | EBV |
| rRNA | 37.00 | 41.92 |
| tRNA | 5.32 | 4.72 |

-continued

| | BL-41 Human Cell Line | |
|---|---|---|
| Type | — | EBV |
| microRNA | 44.36 | 33.94 |
| Repeat | 1.62 | 0.98 |
| Other ncRNA[a] | 4.33 | 5.80 |
| mRNA | 4.11 | 5.39 |
| Viral[b] | 0 | 4.15 |
| Not annotated | 2.26 | 2.23 |
| Not matched. | 0.99 | 0.88 |
| (No. seq.) | (2216) | (1930) |

[a]This includes snRNAs and snoRNAs and other known small cytoplasmic non-coding RNAs.
[b]The annotation for viral sequences is based on EBV B95-8 (GenBank V01555).

TABLE 2

Small RNA sequences derived from viral sequence. The position of the small RNA sequence is given relative to the viral genome sequences specified in Table 1 above.

| Virus | Small RNA Sequence 5' → 3' | Clones | Size range (nt) | Position, Orientation |
|---|---|---|---|---|
| EBV | UAACCUGAUCAGCCCCGGAGUU (SEQ. ID. NO. 1) | 2 | 21-22 | 53762-53783, + |
| | AAAUUCUGUUGCAGCAGAUAGC (SEQ. ID. NO. 17) | 3 | 22 | 55141-55162, + |
| | UAUCUUUUGCGGCAGAAAUUGAA (SEQ. ID. NO. 2) | 50 | 20-23 | 55176-55198, + |
| | UAACGGGAAGUGUGUAAGCACAC (SEQ. ID. NO. 3) | 23 | 19-23 | 55256-55278, + |
| | UCUUAGUGGAAGUGACGUGCU (SEQ. ID. NO. 4) | 1 | 21 | 151640-151660, + |
| | UAUUUUCUGCAUUCGCCCUUGC (SEQ. ID. NO. 5) | 2 | 22 | 153205-153226, + |

Most of the EBV sequences were cloned more than once and the analysis of the genomic sequence flanking the cloned RNAs suggested fold-back structures characteristic of microRNAs genes. The EBV microRNAs originated from 5 different dsRNA precursors that are clustered in two regions of the EBV genome (FIGS. 2A and B).

The EBV microRNAs were all readily detectable by Northern blotting, including the approximately 60-nt fold-back precursor for 3 of the 5 microRNAs (FIG. 2C). The first microRNA cluster is located within the mRNA of the BHFR1 gene encoding a distant Bcl-2 homolog, and we refer to these three microRNAs as miR-BHRF1-1 to miR-BHRF1-3.

miRBHFR1-1 is located in the 5' UTR and miR-BHRF1-2 and -3 are positioned in the 3' UTR of the BHRF1 mRNA. Structurally similar microRNA gene organization has been observed for some mammalian microRNAs that flank open reading frames in expressed sequence tags. The other EBV microRNAs cluster in intronic regions of the BART gene, and we refer to them as miR-BART1 and miR-BART2. Since microRNAs function in RNA silencing pathways either by targeting mRNAs for degradation or by repressing translation, we identified new viral regulators of host and/or viral gene expression.

Example 3

Predicated Target for Epstein Barr Virus Encoded microRNA

EBV latently infected cells can be found in three different latent stages (I to III, FIG. 2A) that are characterized by the expression of various subsets of the latent genes: six nuclear antigens (EBNAs 1, 2, 3A, B, C, and EBNA-LP), three latent membrane proteins (LMPs 1, 2A and 2B), two non-coding RNAs (EBERs 1 and 2) and transcripts from the BamHI A region (BARTs/CSTs) whose coding capacity is still controversial.

We isolated our small RNAs from a latent-stage-III EBV cell line that expresses all latent genes. In order to address if the expression of the EBV microRNAs is coupled with a specific latent stage, we probed for EBV microRNA expression in immortalized cell lines which are in different stages of latency, including Hodgkin's lymphoma (HD, latency II), Burkitt's lymphoma (BL) latency stage I cells, and virus-producing marmoset monkey lymphocytes B95-8 (latency III, with a fraction of 3 to 10% of cells expressing lytic stage antigens) (FIG. 2D).

BART microRNAs were detected in all latent stages consistent with the reported expression of BART during every stage of EBV infection. However, BART microRNA expression was elevated by about 10-fold in the virus producing marmoset cell line (FIG. 2D, lane 9, rows 5 and 6). Although several studies have attempted to identify proteins encoded from the different spliced transcripts of BART, the function of this region remains unknown. Our findings will help to assign a function to the BART region.

The expression pattern of BHRF1 microRNAs is dependent on the EBV latency stage. While cell lines in stage II and III expressed BHRF1 microRNAs (FIG. 2D, lanes 5-6), only one of the two stage I cell lines expressed BHRF1 microRNAs (FIG. 2D, lanes 7, 8). Latency I cell lines are thought to express only EBNA 1, the EBERs and the BARTs.

The expression of a transcript deriving from the BHRF1 region in one of the latency stage I cell lines as well as its expression in stage II cell lines, suggests a new latency stage I/II promoter upstream of the known latency stage I/II Qp promoter (FIG. 2A). A new subdivision of latency I stages may have to be introduced to distinguish between BHRF1 microRNA expressing cell lines in latency I.

Although BHRF1 protein is only detected in lytic stage, latent stage EBV transcripts encompassing the BHRF1 region were observed previously. It is likely that the microRNAs BHRF1-1 to 3 are also expressed during lytic stage along with the BHRF1 protein. The high-level transcription of BHRF1 during the lytic cycle may exceed the cellular microRNA processing capacity and unprocessed transcripts could then be translated.

To identify targets for EBV microRNAs, we used a computational method recently developed for prediction of *Drosophila* microRNAs targets (Enright et al., *Genome Biol.*, 2003, 5:RI, 1). A set of approximately 20,000 non-redundant human 3' UTRs and the genome sequence of EBV were searched for potential microRNA binding sites. The top scoring hits for which a gene function annotation was available, are listed in Table 3. The majority of predicted host cell targets have more than one binding site for the viral microRNA, and approximately 50% of these are additionally targeted by one or several host cell microRNAs. Multiple microRNA binding sites are believed to act synergistically and increase targeting efficiency in a cooperative non-linear fashion.

microRNA modulation of cell proliferation also provides new leads for studying the association of EBV with several cancerous malignancies. Another important group of EBV microRNA targets are B-cell specific chemokines and cytokines, which are important for leukocyte activation and/or chemotaxis. Down-regulation of these genes presumably contributes to escape of EBV-infected B cells from activated cytotoxic T cells. Additional targets include transcriptional regulators and components of signal transduction pathways that are critical for maintaining or switching between EBV lytic and latent stages.

Example 4

EBV Encoded microRNA miR-BART2 Targets Virally Encoded DNA Polymerase BALF5

One of the EBV-encoded microRNAs, miR-BART2, is capable of targeting the virally encoded DNA polymerase BALF5 for degradation (FIG. 3). miR-BART2 is transcribed anti-sense to the BALF5 transcript and is therefore perfectly complementary to the BALF5 3' UTR and able to subject this miRNA for degradation. Similarly, the clustered miRBHRF1-2 and -3 are complementary to the transcript encoding the lytic gene BFLF2 (FIG. 2A), whose function is currently

TABLE 3

Predicted host cell target mRNAs of EBV microRNA. The gene name is indicated as recommended by HUGO, and the gene function annotation was extracted from Ensemble. The number of predicted microRNA binding sites in the 3' UTR of the target gene (NS) and a percentile score ranking the target site predictions (%-ile) are indicated. If human microRNAs are also predicted to bind to a putative EBV microRNA regulated target, it is indicated in the last column. The predicated human microRNA binding sites are also conserved in the orthologous mRNAs in mouse.

| EBV microRNA | Gene ID | Proposed function | NS | %-ile | Human miRNA |
|---|---|---|---|---|---|
| | | Apoptosis, cell proliferation | | | |
| BART1, BHRF1-2 | BCL2 | Apoptosis regulator Bcl-2 | 3, 1 | 100, 98 | miR-217, miR-140 |
| BHRF1-1 | P53 | Tumor suppressor P53 | 2 | 98 | |
| BHRF1-1 | E2F1 | Retinoblastoma Binding protein 3, Transcription factor E2F-1 Transcription regulation | 2 | 98 | miR-20, miR-106 |
| BART1 | HIC2 | Hypermethylated in Cancer 2 Protein | 2 | 99 | |
| BART1 | ZNF177 | Zinc Finger protein 177 | 4 | 100 | |
| BART2 | UBN1 | Ubinuclein 1 | 3 | 100 | |
| BHRF1-1 | CBFA2T2 | Myeloid Translocation gene-related protein 1 | 3 | 100 | miR-301 |
| BHRF1-3 | NSEP1 | Y Box Binding protein | 1 | 94 | miR-95, miR-216, miR-136 |
| BHRF1-3, BART2 | TGIF | 5'-TG-3' Interacting factor, Homeobox protein TGIF | 1, 1 | 97 97 | miR-194 |
| | | Immune response | | | |
| BART2 | LRBA | Lipopolysaccharide-responsive and beige like protein, BCL8 Homolog | 4 | 99 | miR-15a, miR-146 miR-29a |
| BHRF1-1 | LILRB5 | Leukocyte immunoglobulin receptor, subfamily B, member 5 | 2 | 100 | |
| BHRF1-3 | PRF1 | Perforin 1 precursor Signal transduction | 1 | 99 | |
| BART1 | CXCL12 | Stromal cell derived factor 1 precursor, Pre-B growth Stimulating factor | 3 | 100 | miR-106, miR-135 miR-197 |
| BART2 | GAB2 | GRB2- Associated Binding Protein 2 | 4 | 100 | miR-155 |
| BART2 | TNFRSF1A | Tumor Necrosis Factor Receptor Superfamily member 1A | 2 | 99 | |
| BHRF1-2 | PIK3R1 | Phosphatidylinositol 3-kinase regulatory Alpha Subunit | 1 | 92 | let-7b |
| BHRF1-2, BART2 | B7RP-1 | B7 homolog, ICOS ligand precursor | 1, 3 | 97, 99 | miR-155 |
| BHRF1-3 | CXCL11 | Small inducible cytokine B11 precursor, I-TAC Chromosome organization | 3 | 100 | |
| BHRF1-2 | CENPA | Centromere Protein A | 1 | 98 | miR-16 |

Several of the predicted viral microRNA targets are prominent regulators of cell proliferation and apoptosis, which are presumably important for growth control of the infected cells.

unknown. The down-regulation of lytic genes by viral microRNAs may contribute to establishment and maintenance of latent infection.

What we claim is:

1. An isolated single stranded DNA virus microRNA molecule comprising a maximum of fifty moieties, wherein each moiety comprises a base bonded to a backbone unit, said molecule comprising the sequence of bases identified in SEQ ID NOS. 1, 3, or 5.

2. A molecule according to claim 1, wherein the molecule is modified for increased nuclease resistance.

3. An isolated single stranded anti-DNA virus microRNA molecule comprising a maximum of fifty moieties, wherein each moiety comprises a base bonded to a backbone unit, said molecule comprising the sequence of bases identified in SEQ. ID. NOS. 11, 13 or 15, wherein the molecule is capable of inhibiting microRNP activity.

4. A molecule according to claim 3, wherein at least one of the moieties is a deoxyribonucleotide.

5. A molecule according to claim 4, wherein the deoxyribonucleotide is a modified deoxyribonucleotide moiety.

6. A molecule according to claim 5, wherein the modified deoxyribonucleotide is a phosphorothioate deoxyribonucleotide moiety.

7. A molecule according to claim 5, wherein the modified deoxyribonucleotide is N3'→N5' phosphoroamidate deoxyribonucleotide moiety.

8. A molecule according to claim 3, wherein at least one of the moieties is a ribonucleotide moiety.

9. A molecule according to claim 8, wherein at least one of the moieties is a modified ribonucleotide moiety.

10. A molecule according to claim 9, wherein the modified ribonucleotide is substituted at the 2' position.

11. A molecule according to claim 10, wherein the substituent at the 2' position is a $C_1$ to $C_4$ alkyl group.

12. A molecule according to claim 11, wherein the alkyl group is methyl.

13. A molecule according to claim 11, wherein the alkyl group is allyl.

14. A molecule according to claim 10, wherein the substituent at the 2' position is a $C_1$ to $C_4$ alkoxy-$C_1$ to $C_4$ alkyl group.

15. A molecule according to claim 14, wherein the $C_1$ to $C_4$ alkoxy-$C_1$ to $C_4$ alkyl group is methoxyethyl.

16. A molecule according to claim 9, wherein the modified ribonucleotide has a methylene bridge between the 2'-oxygen atom and the 4'-carbon atom.

17. A molecule according to claim 3, wherein at least one of the moieties is a peptide nucleic acid moiety.

18. A molecule according to claim 3, wherein at least one of the moieties is a 2'-fluororibonucleotide moiety.

19. A molecule according to claim 3, wherein at least one of the moieties is a morpholino phosphoroamidate nucleotide moiety.

20. A molecule according to claim 3, wherein at least one of the moieties is a tricyclo nucleotide moiety.

21. A molecule according to claim 3, wherein at least one of the moieties is a cyclohexene nucleotide moiety.

22. A molecule according to claim 3, wherein the molecule comprises at least one modified moiety for increased nuclease resistance.

23. A molecule according to claim 22, wherein the nuclease is an exonuclease.

24. A molecule according to claim 23, wherein the molecule comprises at least one modified moiety at the 5' end.

25. A molecule according to claim 23, wherein the molecule comprises at least two modified moieties at the 5' end.

26. A molecule according to claim 23, wherein the molecule comprises at least one modified moiety at the 3' end.

27. A molecule according to claim 23, wherein the molecule comprises at least two modified moieties at the 3' end.

28. A molecule according to claim 23, wherein the molecule comprises at least one modified moiety at the 5' end and at least one modified moiety at the 3' end.

29. A molecule according to claim 23, wherein the molecule comprises at least two modified moieties at the 5' end and at least two modified moieties at the 3' end.

30. A molecule according to claim 23, wherein the molecule comprises a nucleotide cap at the 5' end, the 3' end or both.

31. A molecule according to claim 23, wherein the molecule comprises a chemical cap at the 5' end, the 3' end, or both.

32. A molecule according to claim 22, wherein the nuclease is an endonuclease.

33. A molecule according to claim 32, wherein the molecule comprises at least one modified moiety between the 5' and 3' end.

34. A molecule according to claim 32, wherein the molecule comprises a chemical cap.

35. A molecule according to claim 3, wherein all of the moieties are nuclease resistant.

36. An isolated microRNP comprising an isolated single stranded DNA virus microRNA molecule according to claim 1.

37. An molecule according to claim 1, further comprising a sequence of bases at the 3' and/or 5' end to form a hairpin precursor from which said microRNA molecule is derived, said hair-pin precursor having SEQ ID NO. 6, 8 or 10.

* * * * *

SEQUENCE LISTING

<160> NUMBER OF SEQ ID NOS: 17

<210> SEQ ID NO 1
<211> LENGTH: 22
<212> TYPE: RNA
<213> ORGANISM: Epstein Bar Virus

<400> SEQUENCE: 1
uaaccugauc agccccggag uu                                              22

<210> SEQ ID NO 2
<211> LENGTH: 23
<212> TYPE: RNA
<213> ORGANISM: Epstein Bar Virus

<400> SEQUENCE: 2 uaucuuugc ggcagaaauu gaa                                              23

<210> SEQ ID NO 3
<211> LENGTH: 23
<212> TYPE: RNA
<213> ORGANISM: Epstein Bar Virus

<400> SEQUENCE: 3
uaacgggaag uguguaagca cac                                             23

<210> SEQ ID NO 4
<211> LENGTH: 21
<212> TYPE: RNA
<213> ORGANISM: Epstein Bar Virus

<400> SEQUENCE: 4
ucuuagugga agugacgugc u                                               21

<210> SEQ ID NO 5
<211> LENGTH: 22
<212> TYPE: RNA
<213> ORGANISM: Epstein Bar Virus

<400> SEQUENCE: 5
uauuuucugc auucgcccuu gc                                              22

<210> SEQ ID NO 6
<211> LENGTH: 66
<212> TYPE: RNA
<213> ORGANISM: Epstein Bar Virus

<400> SEQUENCE: 6
uauuaaccug aucagccccg gaguugccug uuucaucacu aaccccgggc cugaagaggu     60
ugacaa                                                                66

<210> SEQ ID NO 7
<211> LENGTH: 65
<212> TYPE: RNA
<213> ORGANISM: Epstein Bar Virus

<400> SEQUENCE: 7
cuuuuaaauu cuguugcagc agauagcuga uacccaaugu uaucuuugc ggcagaaauu      60 gaaag                                                                 65

```
<210> SEQ ID NO 8
<211> LENGTH: 65
<212> TYPE: RNA
<213> ORGANISM: Epstein Bar Virus

<400> SEQUENCE: 8
ucuaacggga aguguguaag cacacacgua auuugcaagc ggugcuucac gcucuucguu    60
aaaau                                                               65

<210> SEQ ID NO 9
<211> LENGTH: 70
<212> TYPE: RNA
<213> ORGANISM: Epstein Bar Virus

<400> SEQUENCE: 9
cggggucuua guggaaguga cgugcuguga auacaggucc auagcaccgc uaccacuau    60 gucucgcccg                                                          70

<210> SEQ ID NO 10
<211> LENGTH: 62
<212> TYPE: RNA
<213> ORGANISM: Epstein Bar Virus

<400> SEQUENCE: 10
acuauuuucu gcauucgccc uugcgugucc auuguugcaa ggagcgauuu ggagaaaaua   60
aa                                                                  62

<210> SEQ ID NO 11
<211> LENGTH: 22
<212> TYPE: RNA
<213> ORGANISM: Artificial
<220> FEATURE:
<223> OTHER INFORMATION: Anti-Epstein Bar Virus microRNA

<400> SEQUENCE: 11
aacuccgggg cugaucaggu ua                                            22

<210> SEQ ID NO 12
<211> LENGTH: 23
<212> TYPE: RNA
<213> ORGANISM: Artificial
<220> FEATURE:
<223> OTHER INFORMATION: Anti-Epstein Bar Virus microRNA

<400> SEQUENCE: 12
uucaauuucu gccgcaaaag aua                                           23

<210> SEQ ID NO 13
<211> LENGTH: 23
<212> TYPE: RNA
<213> ORGANISM: Artificial
<220> FEATURE:
<223> OTHER INFORMATION: Anti-Epstein Bar Virus microRNA

<400> SEQUENCE: 13
gugugcuuac acacuucccg uua                                           23

<210> SEQ ID NO 14
<211> LENGTH: 21
<212> TYPE: RNA
<213> ORGANISM: Artificial
<220> FEATURE:
<223> OTHER INFORMATION: Anti-Epstein Bar Virus microRNA
```

```
-continued

<400> SEQUENCE: 14
agcacgucac uuccacuaag a                                          21

<210> SEQ ID NO 15
<211> LENGTH: 22
<212> TYPE: RNA
<213> ORGANISM: Artificial
<220> FEATURE:
<223> OTHER INFORMATION: Anti-Epstein Bar Virus microRNA

<400> SEQUENCE: 15
gcaagggcga augcagaaaa ua                                         22

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16 gcagggcca tgctaatctt ctctgtatcg                                  30

<210> SEQ ID NO 17
<211> LENGTH: 22
<212> TYPE: RNA
<213> ORGANISM: Epstein Bar Virus

<400> SEQUENCE: 17
aaauucuguu gcagcagaua gc                                         22
```